United States Patent
Rinck et al.

(10) Patent No.: US 10,799,119 B2
(45) Date of Patent: Oct. 13, 2020

(54) METHOD AND APPARATUS FOR PROVISION OF PREPARATORY INFORMATION FOR MAGNETIC RESONANCE IMAGING

(71) Applicant: Siemens Healthcare GmbH, Erlangen (DE)

(72) Inventors: Daniel Rinck, Forchheim (DE); Verena Gass, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 228 days.

(21) Appl. No.: 15/795,921

(22) Filed: Oct. 27, 2017

(65) Prior Publication Data

US 2018/0116518 A1 May 3, 2018

(30) Foreign Application Priority Data

Oct. 28, 2016 (EP) .................................... 16196323

(51) Int. Cl.
*A61B 5/00* (2006.01)
*G01R 33/28* (2006.01)
(Continued)

(52) U.S. Cl.
CPC ............ *A61B 5/0033* (2013.01); *A61B 5/055* (2013.01); *G01R 33/283* (2013.01); *G01R 33/4808* (2013.01); *G01R 33/56* (2013.01); *G06K 9/6202* (2013.01); *G06T 7/33* (2017.01); *G06T 15/08* (2013.01); *G16H 40/63* (2018.01);
(Continued)

(58) Field of Classification Search
CPC ... A61B 5/0033; A61B 5/0037; A61B 5/1079;
A61B 5/0555; G06T 15/08; G06T 7/521;
G06T 7/33-344; G06T 7/73-75; G16H
40/63; G01R 33/283; G01R 33/4808;
(Continued)

(56) References Cited

U.S. PATENT DOCUMENTS 6,405,072 B1 * 6/2002 Cosman ............... A61B 6/5247
600/426
8,212,558 B2 * 7/2012 Mueller ................ A61B 5/055
324/307
(Continued)

FOREIGN PATENT DOCUMENTS

JP 2004201977 A 7/2004

OTHER PUBLICATIONS

Krempien et al. "Projector-based Augmented Reality for Intuitive Intraoperative Guidance in Image-Guided 3D Interstitial Brachytherapy", Int. J. Radiation Oncology Biol. Phys. vol. 70(3) 2008. p. 944-952 (Year: 2008).*

Primary Examiner — Theodore J Stigell
Assistant Examiner — Sean A Frith
(74) Attorney, Agent, or Firm — Schiff Hardin LLP

(57) ABSTRACT

In a method and apparatus for provision of preparatory information for preparation of magnetic resonance imaging of an examination object, the examination object is supported on a patient support of the magnetic resonance apparatus, a depth map of the examination object supported on the patient support is acquired by a time-of-flight camera, preparatory information for the preparation of the magnetic resonance imaging is generated in a computer using the acquired depth map, and the preparatory information are provided from the computer.

16 Claims, 9 Drawing Sheets

(51) Int. Cl.
- *G06T 7/33* (2017.01)
- *A61B 5/055* (2006.01)
- *G01R 33/48* (2006.01)
- *G01R 33/56* (2006.01)
- *G06T 15/08* (2011.01)
- *A61B 5/107* (2006.01)
- *G01R 33/54* (2006.01)
- *G06T 7/521* (2017.01)
- *G16H 40/63* (2018.01)
- *G06K 9/62* (2006.01)

(52) U.S. Cl.
CPC .......... *A61B 5/0037* (2013.01); *A61B 5/1079* (2013.01); *G01R 33/543* (2013.01); *G01R 33/5608* (2013.01); *G06T 7/521* (2017.01)

(58) Field of Classification Search
CPC .. G01R 33/56; G01R 33/543; G01R 33/5608; G01R 33/00; G06K 9/6202
See application file for complete search history.

(56) References Cited

U.S. PATENT DOCUMENTS

| | | | |
|---|---|---|---|
| 8,390,290 B2* | 3/2013 | Sukkau | G01R 33/3415 |
| | | | 324/318 |
| 8,587,312 B2* | 11/2013 | Biber | G01R 33/3415 |
| | | | 324/318 |
| 2003/0016015 A1 | 1/2003 | Eggers et al. | |
| 2008/0108892 A1 | 5/2008 | Ritter | |
| 2013/0165767 A1* | 6/2013 | Darrow | G01R 33/543 |
| | | | 600/414 |
| 2013/0279779 A1 | 10/2013 | Darrow et al. | |
| 2013/0281818 A1* | 10/2013 | Vija | A61B 6/467 |
| | | | 600/407 |
| 2013/0342851 A1* | 12/2013 | Dresel | G01B 11/24 |
| | | | 356/601 |
| 2015/0293188 A1* | 10/2015 | Haider | G01R 33/34007 |
| | | | 324/307 |
| 2015/0327831 A1* | 11/2015 | Levin | A61B 5/0037 |
| | | | 600/427 |
| 2016/0300343 A1* | 10/2016 | Gazit | G06T 7/11 |
| 2017/0082716 A1* | 3/2017 | Greiser | G01R 33/283 |
| 2018/0014745 A1 | 1/2018 | Senegas et al. | |

* cited by examiner

METHOD AND APPARATUS FOR PROVISION OF PREPARATORY INFORMATION FOR MAGNETIC RESONANCE IMAGING

BACKGROUND OF THE INVENTION

Field of the Invention

The present invention concerns a method for provision of preparatory information to prepare for magnetic resonance (MR) imaging of an examination object by operation of a magnetic resonance apparatus, as well as a magnetic resonance apparatus and a storage medium encoded with programming instructions for implementing such a method.

Description of the Prior Art

In a magnetic resonance apparatus, also referred to as a magnetic resonance tomography system, the body of an object to be examined, for example a patient, a healthy test subject, an animal or a phantom, is exposed to a relatively high basic magnetic field, for example of 1.5 or 3 or 7 Tesla, produced by a basic field magnet of an MR data acquisition scanner. In addition gradient fields are applied by a gradient coil arrangement. Radio-frequency pulses (excitation pulses) are then radiated by a suitable radiator via a radio-frequency antenna arrangement, which leads to the nuclear spins of specific atoms, which are resonantly excited by this radio-frequency field, being deflected by a defined flip angle in relation to the magnetic field lines of the basic magnetic field. During the relaxation of the nuclear spins, radio-frequency signals, called magnetic resonance signals, are emitted, which are received by suitable radio-frequency antennas and are then further processed. Finally, the desired image data can be reconstructed from the raw data acquired in this manner.

The preparation for magnetic resonance imaging, such as the placement of at least one local coil and/or the supporting of the examination object on the patient support of the magnetic resonance scanner, can require long periods of time. Therefore, automations and/or options for assisting the operator (medical technician) of the MR apparatus in the preparation of the magnetic resonance imaging are desirable. For example, methods for automatic recognition of the position of the at least one local coil and/or optimization of the positioning of the examination object can be of great interest.

In such cases, it can be desirable, even before the start of the magnetic resonance imaging, to be able to check the position of the at least one local coil, in order to be able to carry out an optimization of the position as needed. For this purpose, it is important to identify the position of the at least one local coil with a high accuracy. Sensors for detection of the position of the local coil, such as B0 Hall sensors, ultrasound sensors, RFID tags, and encoding of the coils via embedded materials with specific magnetic resonance contrast, are known. These known sensors, however, usually provide specifications only with regard to a point position of the at least one local coil. In most cases, the alignment and/or the deformation of the at least one local coil in the space for the examination object, particularly with flexible coils, cannot be detected with these known sensors, particularly when only one known sensor is used.

It can also be desirable, during the preparation of the magnetic resonance imaging, to automatically determine a localization of an organ to be examined in the examination object. Usually the region of the body to be examined, which approximately contains the organ to be examined, is positioned with a laser cross while the subject is at a front side of the magnetic resonance scanner, the patient being subsequently moved automatically into an isocenter of the magnetic resonance scanner. The organ to be examined is thus positioned manually, and during the positioning, the organ to be examined is typically not visible or is difficult to make out by touch.

This problematic situation can arise, for example, during the preparation for examination of the prostate of the examination object. Usually only the iliac crest of the examination object is available as a landmark that can be felt for the positioning of the prostate. Therefore an experienced operator is required to carry out manual positioning in this case. Since the at least one local coil, which is provided for receiving the magnetic resonance signals from the prostate, has only a limited reception profile (field of view), it can be necessary to position the at least one local coil as close as possible to the prostate.

SUMMARY OF THE INVENTION

An object of the invention is to provide an advantageous preparation for magnetic resonance imaging.

The inventive method for provision of preparatory information for preparation for magnetic resonance imaging of an examination object by operation of a magnetic resonance apparatus has the following steps. The examination object is supported on a patient support of the scanner of the magnetic resonance apparatus. A depth map of the examination object supported on the patient support is acquired by a time-of-flight camera. Preparatory information for the magnetic resonance imaging is generated in a computer using the acquired depth map, and the generated preparatory information is provided in electronic form as an output of the computer.

The acquisition of the depth map and the generation and provision of the preparatory information take place in the time after the examination object has been supported on the patient support of the magnetic resonance apparatus. The examination object is supported on the patient support so that the magnetic resonance imaging of the examination object can be carried out after the examination object has been positioned in an isocenter of the magnetic resonance scanner by moving the patient support into the isocenter. Naturally, there can also be a re-positioning of the examination object on the patient support between individual method steps. After the re-positioning of the examination object, a renewed acquisition of the depth map and/or a renewed establishment and provision of the preparatory information may be warranted.

The depth map is acquired from the examination object in the time before the positioning of the examination object in the isocenter of the magnetic resonance scanner. The depth map is thus acquired while the examination object is still positioned at least partly outside the tunnel-shaped opening of the magnetic resonance scanner. Similarly, the preparatory information can be established and provided in the time before the positioning of the examination object in the isocenter of the magnetic resonance apparatus. Naturally, for specific applications, it is also conceivable for the depth map to be acquired in the time after the positioning of the examination object in the isocenter of the magnetic resonance scanner, for example in order to allow a further monitoring of the examination object during the magnetic resonance imaging, particularly when the examination object has been moved into the magnetic resonance scanner with his or her feet pointing forward (feet-first examination). The preparatory information can also be acquired, established and/or provided in the time after the positioning of the examination object in the isocenter of the magnetic resonance scanner.

The time-of-flight camera can acquire a three-dimensional depth map of the examination object. Such a depth map can then include a two-dimensional matrix, which encodes the distance from the mapped scene to a point or to a plane associated with the time-of-flight camera. Therefore, the depth map is composed of mage points that encode a distance between the mapped object and the time-of-flight camera. With a suitable calibration of the time-of-flight camera, the image points of the depth map can be stored or displayed in physical distance units, such as meters. When the depth map is displayed, for example as a grayscale image, an object positioned closer to the time-of-flight camera, possibly a local coil positioned on the examination object, will appear darker in the depth map than an image element that is farther away, for example an edge area of the examination object and/or a surface of the patient support and/or a floor of the examination room. The depth map thus maps a surface of the examination object and possibly other objects positioned on the examination object, such as a local coil or a blanket, in detail.

The time-of-flight camera, which is used for acquisition of the depth map, can include a suitable depth sensor. As examples, a few possible depth sensors for the time-of-flight camera are: a time-of-flight sensor (TOF sensor), a stereo triangulation sensor or set-up with a number of cameras, and a sensor that recognizes a structured light pattern that is projected onto the examination object (for example infrared light, as with the Microsoft Kinect camera). Embodiments of these depth sensors and further possible depth sensors are known to those skilled in the art, so such depth sensors need not be discussed in any greater detail herein.

The time-of-flight camera is positioned in the examination room in which the magnetic resonance scanner is also situated. For the acquisition of the depth map, the time-of-flight camera is preferably positioned directly above the patient support, when the patient support is situated outside the tunnel-shaped opening of the magnetic resonance scanner. In this case, the time-of-flight camera can be mounted on the ceiling of the examination room. The time-of-flight camera can in this way acquire the depth map of the examination object perpendicularly from above. Naturally an oblique or offset positioning of the time-of-flight camera is also possible. Other mountings of the time-of-flight camera in the examination room, for example on a wall and/or on a stand and/or movable mountings, are conceivable.

The acquisition of the depth map of the examination object can be of the examination object alone, or of the examination object together with at least one other item, which is positioned in close vicinity of the examination object. The at least one further item can be at least one local coil, which is provided for receiving magnetic resonance signals during the magnetic resonance imaging of the examination object. The depth map thus maps the examination object together with the at least one local coil. The at least one further item can also be a support aid and/or a blanket. It is also possible for the depth map to map only the at least one local coil. In general, the time-of-flight camera thus acquires the depth map of an examination scene, which can include the examination object and/or the patient support and/or at least one item, such as the at least one local coil. The time-of-flight camera can additionally acquire an RGB image and/or an infrared image of the examination scene. The RGB image and/or infrared image can then likewise be used for establishing the preparatory information, for example using an edge detection of the at least one local coil in the RGB image and/or in the infrared image.

The preparatory information is generated by an establishment algorithm executed in the computer, which uses as its input parameters the acquired depth map and/or information derived from the acquired depth map, and produces the preparatory information as its output parameters. Naturally further input parameters considered sensible to those skilled in the art can be included in the establishment of the preparatory information. The preparatory information is related to the preparation of the magnetic resonance imaging of the examination object. For example, the provision of the preparatory information can assist and/or simplify and/or automate the preparation of the magnetic resonance imaging. The preparation of the magnetic resonance imaging as used herein means actions that occur in the time before the start of the acquisition of the magnetic resonance signals, in particular in the time before the positioning of the examination object in the isocenter of the magnetic resonance scanner. For example, the preparation of the examination object can be the correct supporting of the examination object on the patient support and/or a suitable positioning of at least one local coil on the examination object. The preparatory information can be related in an examination-specific manner to these actions.

The provision of the preparatory information can be an output of the preparatory information, for example on a display screen and/or by a projector and/or by an audio device. As an alternative or in addition the provision of the preparatory information, the preparatory information can be stored in a database. As an alternative or in addition the provision of the preparatory information, a transfer of the preparatory information to a computer can take place, which can control the preparation of the magnetic resonance imaging automatically and/or semi-automatically on the basis of the preparatory information.

In this way the preparatory information provides valuable additional information for the preparation of the magnetic resonance imaging, or can contribute to at least a part of the preparation of the magnetic resonance imaging being done automatically. In such cases, the acquired depth map provides valuable depth information as a basis for the creation of the preparatory information. For example, the inventive method can facilitate the preparation of the magnetic resonance imaging of the examination object by less well-trained or inexperienced personnel. The preparatory information can also make it possible to carry out the preparation of the magnetic resonance imaging in a standardized manner with consistent quality, particularly for less experienced operating personnel.

In an embodiment, the establishment of the preparatory information includes computation of a probability of localizing an organ to be examined in the magnetic resonance imaging in a body of the examination object, using the depth map.

An noted, for the magnetic resonance imaging, the organ to be examined should be positioned in the isocenter of the magnetic resonance scanner. The organ to be examined is defined by a diagnostic issue, which is to be clarified by the magnetic resonance image data acquired by the magnetic resonance imaging. If, for example, the magnetic resonance image data are to be used for a staging or a detection of a prostate carcinoma, then the organ to be examined is the prostate of the examination object. The magnetic resonance image data acquired in the magnetic resonance imaging should accordingly primarily map the organ to be examined, and possibly surrounding organ structures. The organ to be examined can also be a body region of the examination object, for example head region, a thorax region or a back region of the examination object.

The probability of localization can be a probability distribution of a spatial localization of the organ to be examined in the body of the examination object. The probability of localization can also be information about the position having the highest probability of location of the organ to be examined in the body of the examination object. The probability of localization can accordingly provide information as to the position at which, in the actual event, the organ to be examined is most probably located in the body of the examination object. In this way, the probability of localization can also be referred to as the probability of presence of the organ to be examined. In this case, the probability of localization is preferably computed in relation to a fixed coordinate system, for example the coordinate system of the magnetic resonance scanner and/or of the patient support and/or of the time-of-flight camera. The probability of localization can also be computed in relation to a coordinate system that is assigned to the examination object, for example by landmarks.

The acquired depth map can be used especially advantageously for computing the probability of localization. Thus, contours of a surface of the examination object can be recognized in the depth map, on the basis of which the probability of localization of the organ to be examined is computed. For this purpose, as will be described in greater detail below, a body model can be matched to the examination object using the depth map. The computed probability of localization relative to such body model can be provided as the preparatory information. Different options for doing this are described below.

In another embodiment, the computation of the probability of localization of the organ to be examined involves a matching of the body model, which represents information about the localization of the organ to be examined in the body model, to the examination object while using the depth map.

The body model, also called an avatar model, can be a three-dimensional body model. The body model can be a standard model of a human body, which is generated, for example, based on an averaging over a number of objects differing from the examination object. For generation of the body model, recourse can be made to larger data databases, which include modelings of the human body in slice recordings. In this way, the body model can represent a "standard person." The body model can also be selected based on patient-specific parameters, such as the gender and/or size and/or age and/or weight of the examination object, from a number of possible body models, or matched using the standard model as a starting point. Registration of the examination object for the magnetic resonance imaging thus can be automated at least in part.

The body model can include contour information of the human body, so that the matching of the body model to the examination object involves a reconciliation of the contour information of the body model to a surface of the examination object recognized in the depth map. As an alternative or in addition, landmarks identified in the depth map can be used for matching of the body model, in which these landmarks are likewise defined, to the examination object. For example a shoulder joint, a hip, a knee, a hand, an elbow etc. can be defined as landmarks in the body model. The matching of the body model to the examination object can accordingly be undertaken based on a matching of the landmarks of the body model to the landmarks identified in the depth map. For this purpose, the body model can be divided into a number of body segments, so there can be an individual matching of the number of body segments to the examination object. Further matching methods are naturally conceivable. On the basis of the matching of the body model to the examination object, an identification of a body surface of the examination object can be made in the depth map. Through the matching of the body model to the examination object, the individual anatomy of the examination object can be taken into account. For the matching of the body model to the depth map, the depth map is recorded before positioning of a component, such as a local coil, on the examination object.

The information about the localization of the organ to be examined in the body model, which is encompassed by the body model, can be stored in relation to the contour information and/or landmarks of the body model. In this way, based on the matching of the body model to the examination object, the information about the localization of the organ to be examined in the body model can be matched to the patient-specific circumstances of the examination object. In this way, the probability of localization of the organ to be examined can be computed especially easily based on the matching of the body model. The information about the localization of the organ to be examined in the body model, which is matched specifically to the examination object during the matching of the body model, thus represents an especially advantageous basis for computing the probability of localization of the organ to be examined in the body of the examination object.

Furthermore, the body model matched to the examination object can form a basis for automatic or semi-automatic determination of at least one patient-specific and/or examination-specific parameter. The at least one such parameter can be, for example, an orientation of the examination object on the patient support and/or a size of the examination object and/or a weight of the examination object. The at least one parameter, after being determined, can be transferred automatically to a control computer of the magnetic resonance apparatus, so manual entry of the at least one parameter can be dispensed with. In this way the matching of the body model to the examination object can fulfill an advantageous double function, namely be used simultaneously for computing the probability of localization of the organ to be examined, and for determining the at least one patient-specific and/or examination-specific parameter.

In an embodiment, the provision of the preparatory information is a display of display data, which are created based on the probability of localization of the organ to be examined, on a display screen, together with a display of a representation of a human body.

The display screen is preferably situated in the examination room in which the magnetic resonance apparatus and the time-of-flight camera are also located. The display screen can be mounted to the magnetic resonance apparatus, in particular the patient support. As an alternative or in addition, the display screen can be a touch interface, which is in communication by a wired connection or wirelessly with the magnetic resonance apparatus.

The representation of the human body can be generated so as to be specific to the examination object, for example on the basis of patient-specific parameters and/or the acquired depth map. The display data can include information as to the point at which, in relation to the representation of the human body, there is the highest probability of localization of the organ to be examined. As an alternative or in addition, it is also conceivable for a confidence radius for the probability of localization of the organ to be examined on the representation of the human body to be displayed as the display data, as will be described in greater detail below in the context of projection data.

In another embodiment, the probability of localization is presented as a projection of projection data, which are created based on the probability of localization of the organ to be examined, onto a body surface of the examination object by a projector.

The projector is preferably situated in the examination room in which the magnetic resonance apparatus and the time-of-flight camera are also located. The projector can be installed in close proximity to the time-of-flight camera and/or can be in a combined facility with the time-of-flight camera. The projector can be mounted at the ceiling of the examination room, preferably perpendicularly above the patient support. The projector is designed to project the projection data onto the examination object and/or onto the patient support. For this purpose, the projector can be, for example, a laser projector, or another type of projector considered sensible to those skilled in the art.

The projection data can include information about the point, in relation to the body of the examination object, at which there is the highest probability of localization of the organ to be examined. In this way, the highest probability of localization of the organ to be examined can be projected directly onto the corresponding point on the surface of the examination object. The projection data can be projected in such cases onto the surface of the body of the examination object corresponding to the organ to be examined. It is also conceivable for the projection data to designate a suitable position for a local coil to receive magnetic resonance signals from the organ to be examined, with the suitable position for the local coil being established on the basis of the probability of localization of the organ to be examined.

The display data and/or projection data thus can provide valuable information about the point at which a local coil must be positioned for receiving magnetic resonance signals from the organ to be examined. The display data and/or projection data can also provide valuable information for positioning the organ to be examined in the isocenter of the magnetic resonance scanner.

In an embodiment, at least one confidence radius is projected onto the body surface of the examination object in the projection data, wherein the at least one confidence radius designates the probability of localization of the organ to be examined.

The confidence radius can identify a region on the body surface of the examination object at which there is a high probability of localization of the organ to be examined. To determine the confidence radius, the spatial distribution of the probability of localization of the organ to be examined can be compared, for example, with a threshold value for the probability of localization. It is also conceivable for a number of confidence radii to be projected onto the body surface of the examination object, which respectively correspond to different magnitudes of the probability of localization of the organ to be examined. Thus a first confidence radius and a second confidence radius can be projected, wherein the first confidence radius delimits a region with the highest probability of localization of the organ to be examined, and the second confidence radius delimits a region with a lower (but still meaningful) probability of localization of the organ to be examined. The projection of the at least one confidence radius can make possible an especially informative representation of the localization of the organ to be examined.

In another embodiment, the patient support of the magnetic resonance apparatus is moved on the basis of the probability of localization, such that the organ to be examined will automatically be positioned in the isocenter of the magnetic resonance scanner for the magnetic resonance imaging.

The patient support will then be moved only when further preparation of the magnetic resonance imaging is concluded, for example after a local coil for acquisition of the magnetic resonance signals has been positioned at a suitable position. The automatic positioning of the organ to be examined in the isocenter of the magnetic resonance scanner can be initiated automatically or manually by an operator, for example by actuation of a switch, making an entry in a touch interface, or by gesture control. The patient support can then be moved such that the region with the highest established probability of localization of the organ to be examined is positioned in the isocenter of the magnetic resonance scanner.

The positioning of the organ to be examined in the isocenter of the magnetic resonance scanner is important, in order for high-quality magnetic resonance image data to be acquired from the organ to be examined in the magnetic resonance imaging. The automatic positioning of the organ to be examined in the isocenter of the magnetic resonance scanner can facilitate or accelerate the preparation of the magnetic resonance imaging. The known manual positioning of the organ to be examined using a laser cross can accordingly be omitted. This conventional technique lead to incorrect positionings, since the anatomy of the examination object is frequently covered by items such as a local coil or a blanket. For this reason, in manual positioning using a laser cross, it is often the case for a local coil positioned on the examination object to be used as a reference object. If, however, the center of this local coil does not lie exactly above the organ to be examined, then, in such manual positioning, the organ to be examined may not be positioned directly in the isocenter of the magnetic resonance scanner. Using the inventive automatic procedure, a correct positioning of the organ to be examined in the isocenter of the magnetic resonance scanner is insured, even for an operator with little experience.

In another embodiment, the acquired depth map thus maps a local coil, which is provided for receiving magnetic resonance signals during magnetic resonance imaging of the examination object, and the generation of the preparatory information includes establishing the position of the local coil on the basis of the depth map.

The local coil provided for receiving the magnetic resonance signals is selected for the magnetic resonance examination by operating personnel dependent on the area of the body of the examination object to be examined. Such a local coil receives magnetic resonance signals with a higher signal-to-noise ratio (SNR) compared to a body coil installed permanently in the magnetic resonance scanner, because it is positioned closer to the region of the body of the examination object to be examined. Different variants of such a local coil are available, for example a head coil, as a shoulder coil, as a knee coil, etc. (wherein "coil" also encompasses a coil array of multiple individual coils).

Such a local coil can be positioned at any of a number of locations in relation to the examination object or to the patient support. For example, the local coil can be a flexible head antenna, which can be positioned at different positions on the examination object and can also assume different shapes. Then the establishment of the position of the flexible head antenna can additionally also include establishing the shape of the flexible head antenna.

The depth map is preferably acquired when the local coil has already been placed by the operating personnel on the region of the body of the examination object to be examined. The acquired depth map then serves as a basis for establishing the position of the local coil. The local coil typically stands out in the depth map from the body surface of the examination object. The position of the local coil thus can be recognized especially easily in the depth map. The provision of the preparatory information can then include provision of the position of the local coil. The recognized position of the local coil can be used in a suitable manner for supporting the preparation of the magnetic resonance imaging.

In specific application cases, the recognized position of the local coil can be used for automatic detection of potential collisions of parts of the local coil with other components of the magnetic resonance scanner, for example the edge or wall of the tunnel-shaped opening of the magnetic resonance scanner. When such a potential collision is detected, a warning can be emitted to the operating personnel, and/or movement of the patient support can be stopped or slowed. It is also conceivable in specific application cases for the position of the local coil to be recognized using deep-learning methods on the basis of the depth map.

In another embodiment, the acquisition of the depth map includes acquisition of a first depth map in the time before positioning the local coil for the magnetic resonance imaging, and acquisition of a second depth map in the time after positioning the local coil for the magnetic resonance imaging, and the establishment of the position of the local coil is done by determining differences between the first depth map and the second depth map.

As noted, the positioning of the local coil for the magnetic resonance imaging involves placing the local coil provided for receiving the magnetic resonance signals on a region of the body of the examination object to be examined by operating personnel. The first depth map will continue to be acquired after placing the examination object on the patient support. In this way the second depth map can have depth information from the local coil positioned on the examination object, such depth information from the local coil not yet being present in the first depth map.

Accordingly, by the determination of the differences (or a difference) between the first depth map and the second depth map, information can be obtained from which the position of the local coil is able to be established. The determination of the differences between the first depth map and the second depth map can be done by generating a difference map between the first depth map and the second depth map. The local coil can then be isolated in this difference map. A possible process for doing this is described in the embodiment below.

In this embodiment, the establishment of the position of the local coil is done by matching a geometrical model of the local coil to the differences between the first depth map and the second depth map.

If a difference map is formed between the first depth map and the second depth map, then the geometrical model of the local coil can be matched to the difference pixel cloud, which is produced at the position of the local coil in the difference map. For this purpose, features of the difference pixel cloud, such as a center of gravity and/or primary axes, can be established for matching the geometrical model of the local coil. There can also be a pre-processing of the difference map using different methods, for example a threshold value operation, a clustering operation, a region-growing method, a morphological dilatation or erosion, etc.

The geometrical model can be selected depending on the type of local coil that is used. The type of local coil to be used can be read out from coil files, which are produced on the basis of the plug-in mounting of the local coil to the patient support. The geometrical model is then loaded into a processor from a database for recognizing the position of the local coil. The geometrical model of the local coil can be a three-dimensional CAD model or wireframe model, and can be based, for example, on production data or image data of the local coil. The use of the wireframe model allows structural information about the local coil to be taken into account, which can be assigned to the spatial positions. In other cases, the geometrical model of the local coil can be a pure point cloud or vertices (planes through three points including a normal to the plane).

The matching of the geometrical model of the local coil to the differences between the first depth map and the second depth map can be done by an optimization method considered appropriate to those skilled in the art, which uses a minimization of a distance scale. For example, a point-matching method or iterative optimization method can be used. The geometrical model of the local coil can be matched by minimization of a distance scale between the geometrical model and the differences between the first depth map and the second depth map. In the matching of the geometrical model, further characteristics of the local coil, for example flexibility of the local coil and/or boundary conditions, which result from the shape of the local coil, can also be taken into account.

Overall, such a process allows an especially robust recognition of the position of the local coil on the basis of the acquired depth maps. Because of the restriction of the search area, such a process can also recognize the position of the local coil in an especially high-performance manner.

In another embodiment, the positions of a number of local coils, which are provided for acquisition of the magnetic resonance signals during the magnetic resonance imaging of the examination object, are established on the basis of the depth map. For the establishment of the positions of the number of local coils, different markers, which are respectively attached to a surface of each of the multiple local coils, are recognized in an image acquired by the time-of-flight camera.

The markers in this case can be optical markers, which can be recognized in a conventional optical image, which is acquired by the time-of-flight camera. The markers are designed so that they individually appear differently in the image acquired by the time-of-flight camera. For example, the markers can be different colors. An option is for the different markers to respectively reflect infrared light to different degrees, so the different markers are individually recognizable in an infrared image acquired by the time-of-flight camera. This process can make it easier to carry out a separation of the number of local coils in the depth map, for example in the difference pixel cloud between the first depth map and the second depth map. For example, the use of the different markers allows an assignment of a position and/or a geometry of a local coil, among the number of local coils, to the matching coil identification in the system.

In another embodiment, the establishment of the position of the local coil is done using a body model, which is matched to the examination object, wherein, for establishing the position of the local coil, differences between the depth map and the body model matched to the examination object are determined.

The body model can be matched in this case to the examination object using a further depth map, which is acquired from the examination object before the positioning of the local coil. It is, however, advantageous for the body model to be matched to the examination object using a depth map that is acquired from the examination object after the positioning of the local coil. The body model will then be matched to the examination object on the basis of landmarks that are not hidden by the local coil positioned on the examination object.

In this version of this embodiment, the differences between two depth maps will thus not be determined. Instead, the body model matched to the examination object provides a reference body surface, from which the surface of the local coil acquired in the depth map stands out. The differences between the position of the body surface of the body model matched to the examination object and the surface of the local coil can thus be used for establishing the position of the local coil. A model of the local coil can be matched to the differences, analogously to the process just described, for determining the position of the local coil. In this embodiment, the position of the local coil can be determined using just one acquired depth map.

In another embodiment, the establishment of the preparatory information is done by a comparison between the established position of the local coil and a desired position for the local coil for receiving magnetic resonance signals from the organ to be examined. The desired position for the local coil is established on the basis of the calculated probability of localization of the organ to be examined.

In this way, the probability of localization of the organ to be examined in the magnetic resonance imaging in a body of the examination object is computed using the depth map. Furthermore, likewise using the depth map, in particular using the aforementioned first depth map and second depth map, the position of the local coil, which is provided for receiving magnetic resonance signals during the magnetic resonance imaging of the examination object, is established. In this way the comparison of the established position of the local coil with the desired position for the local coil, which is established on the basis of the computed probability of localization of the organ to be examined, is possible. In this way, both the computed probability of localization of the organ to be examined and also the established position of the local coil are included as input parameters in the establishment of the preparatory information.

The desired position of the local coil is established on the basis of a highest probability of localization of the organ to be examined in the body of the examination object. The desired position of the local coil can be defined as being when a center of the local coil is positioned on the body surface of the examination object as perpendicularly as possible directly above the position in the body of the examination object at which the highest probability of localization of the organ to be examined has been established. The desired position of the local coil can be computed such that the local coil, during a positioning at the desired position, is especially suited during the magnetic resonance imaging for receiving magnetic resonance signals from the organ to be examined. In the establishment of the desired position of the local coil, in addition to the probability of localization of the organ to be examined, a reception profile of the local coil can be taken into account.

The comparison between the established position of the local coil and the desired position of the local coil can involve establishment of a degree of matching between the established position of the local coil and the desired position of the local coil. As an alternative or in addition, the comparison between the established position of the local coil and the desired position of the local coil can comprise an establishment of a direction, in particular of a translation direction and/or an angle of rotation, in which the local coil must be shifted and/or rotated, so that the local coil is relocated from the established position to the desired position. Results from the comparison between the established position of the local coil and the desired position of the local coil can be suitably provided as preparatory information, for example output on a display screen.

Compared to known sensors for detection of the position of the local coil, such as B0 Hall sensors, ultrasound sensors, RFID tags, by the time-of-flight camera, the probability of localization or the organ can be computed and the position of the local coil can be recognized at the same time. In this way, the two recognition steps can advantageously be carried out with the same sensor, namely the time-of-flight camera. A synergy effect is accordingly produced by use of the depth map twice for different recognition steps. In this way, the acquisition of the depth map offers an especially advantageous basis for establishing the preparatory information based on the probability of localization of the organ to be examined and the established position of the local coil.

The comparison between the established position of the local coil and the desired position for the local coil can include taking into account a reception profile of the local coil, wherein the reception profile of the local coil is established on the basis of the geometrical model of the local coil. For this purpose, information about the reception profile of the local coil is stored for the geometrical model of the local coil. The reception profile of the local coil can be stored in relation to the wireframe model of the local coil. During the matching of the geometrical model of the local coil to the differences between the first depth map and the second depth map, the information about the reception profile of the local coil can also be matched to the current circumstances. In this way, the reception profile of the local coil can be taken into account in an especially suitable manner in the establishment of the desired position of the local coil.

The reception profile of the local coil can also be simulated by a body model matched to the examination object. In this case, the body model matched to the examination object can provide information about a localization of organs and the associated tissue characteristics. This information can be used for simulation of the reception profile of the local coil actually present during the examination.

In another embodiment, the provision of the preparatory information to be an output of a suggestion for repositioning the local coil based on a result of the comparison.

The suggestion for repositioning is presented as an output on a display screen, which can also be designed as a touch interface. The suggestion for repositioning can also be presented as an output by the projector already described. Further output options for the suggestion for repositioning of the local coil, for example via a haptic unit or an audio output unit, are likewise conceivable.

If the result of the comparison between the established position of the local coil and the desired position of the local coil is that the local coil is already located at the desired position, then the information presented as an output can be that repositioning of the local coil is no longer necessary or that the local coil is located at the desired position. Otherwise, a move instruction can be provided as an output to the operating personnel for implementing the suggestion for repositioning of the local coil. For example, a shift vector can be displayed, by the projector or on the display screen, to enable the local coil to be shifted correctly from the current established position to the desired position. Also, the suggestion can be for a rotation and/or deformation of the local coil that is still needed. The suggestion for repositioning of the local coil can also be provided as output supplied to a further processor, which can control the repositioning of the local coil automatically or semi-automatically.

Overall, the suggestion for repositioning of the local coil offers an especially suitable way to insure the correct position of the local coil for receiving the magnetic resonance signals from the organ to be examined. When non-visible anatomy of the operating object is present, or when inexperienced personnel are carrying out the preparation of the magnetic resonance imaging, this preparatory information can lead to a marked increase in the quality of the preparation of the magnetic resonance imaging.

The invention also encompasses a magnetic resonance apparatus with a patient support, a time-of-flight camera, an output interface and a computer, wherein the apparatus is configured to implement any or all embodiments of the inventive method. In this way, the inventive apparatus for implementing the method for provision of preparatory information is designed for preparation of magnetic resonance imaging of an examination object by means of a magnetic resonance apparatus.

In this case, the computer can be used to control other components of the apparatus. Also, the computer is configured to execute computer-readable instructions, in order to implement the inventive method or to undertake control of the execution of the inventive method. The computer thus has a memory, wherein computer-readable information is stored. The computer is configured to load the computer-readable information from the memory and to execute the computer-readable information, in order to implement the inventive method.

The components of the computer can be embodied primarily as software components. Some of these components, particularly when especially fast computations are needed, can also be realized in the form of software-supported hardware components, for example FPGAs or the like. Likewise the interfaces needed, for example when only a transfer of data from other software components is needed, can be embodied as software interfaces, but they can also be embodied as hardware interfaces, which are activated by suitable software. Naturally it is also conceivable for a number of these components to be realized combined as individual software components or software-supported hardware components.

The apparatus is configured to operate so that, in a first step, the examination object is supported on a patient support of the apparatus. The time-of-flight camera is subsequently operated to acquire a depth map of the examination object supported on the patient support. The computer then generates preparatory information for the preparation of the magnetic resonance imaging using the acquired depth map. The output interface then provides the preparatory information.

The present invention also encompasses a non-transitory, computer-readable data storage medium encoded with programming instructions (program code) that, when the storage medium is loaded into a computer or computer system of a magnetic resonance imaging apparatus, cause the computer or computer system to operate the magnetic resonance imaging apparatus in order to implement any or all embodiments of the method according to the invention, as described above.

Examples of electronically-readable data media are a DVD, a magnetic tape, a hard disk or a USB stick, on which electronically-readable control information, in particular software (cf. above) is stored.

The advantages of the inventive apparatus and the inventive storage medium essentially correspond to the advantages of the inventive method, as described in detail above. Features, advantages and alternate embodiments described above are likewise applicable to the other aspects of the invention. The functional features of the method are implemented by corresponding physical modules, in particular by hardware modules.

DESCRIPTION OF THE PREFERRED EMBODIMENTS

Figure 1:
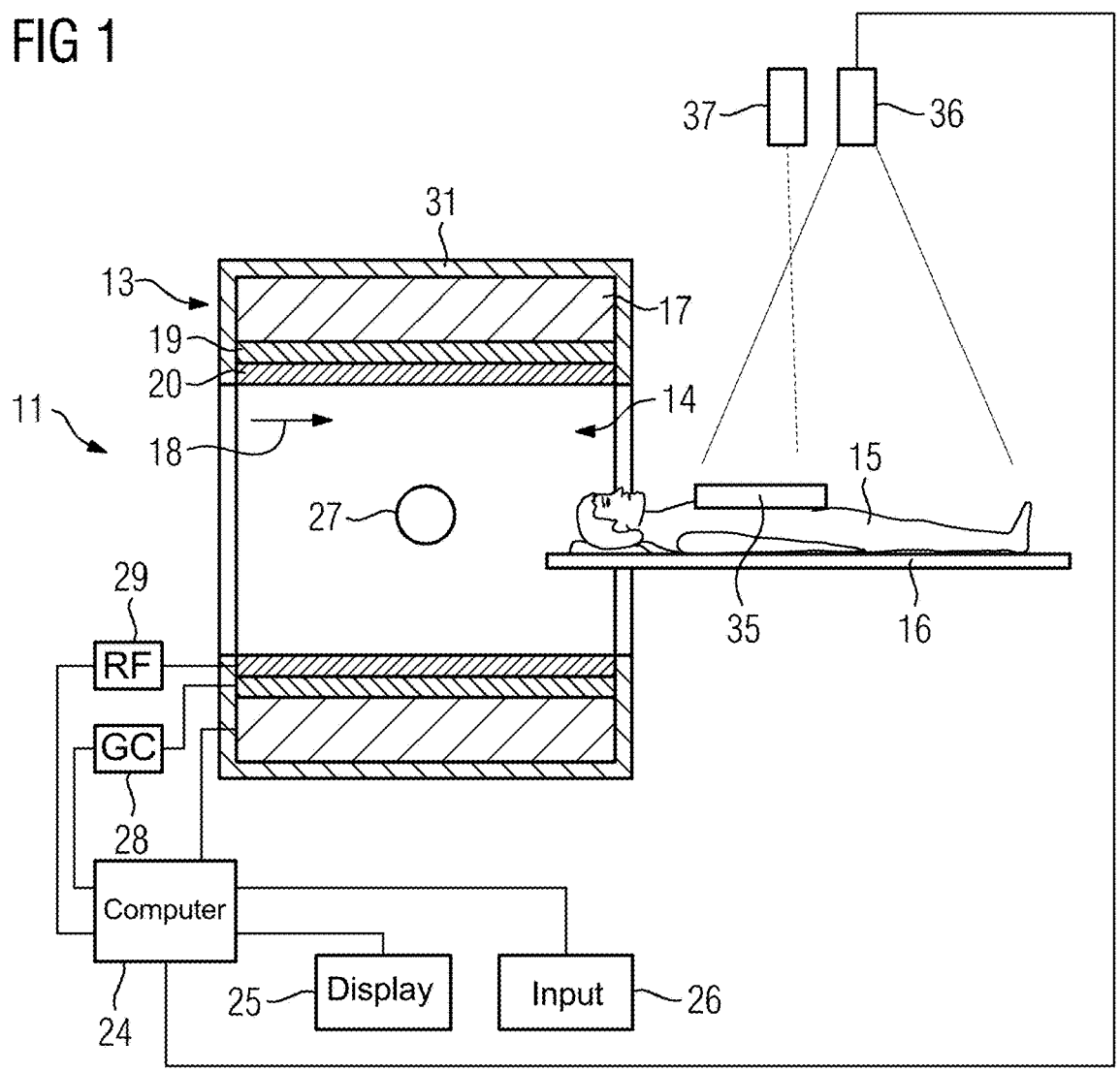
FIG. 1 is a block diagram and schematic illustration of a magnetic resonance imaging apparatus constructed and operating in accordance with the present invention.

FIG. 1 shows the inventive apparatus schematically.

The magnetic resonance apparatus 11 shown in FIG. 1 has a scanner 13 with a basic field magnet 17 that produces a strong, particular constant basic magnetic field 18. The basic magnetic field 18 has an approximately spherical region of high homogeneity, referred to as the isocenter 27. The scanner 13 has a cylindrical patient receiving area 14 for receiving an examination object 15, in the present case a patient. The patient receiving area 14 is surrounded circumferentially by the scanner 13 in a cylindrical shape. The patient 15 can be moved by a patient support 16 into the patient receiving area 14, in particular into the isocenter 27. To this end the patient support 16 has a table that is movable within the scanner 13. The scanner 13 is screened from the outside by a housing shell 31.

The scanner 13 further has a gradient coil arrangement 19 that generates magnetic field gradients, which are used for spatially encoding the MR signals during imaging. The gradient coil arrangement 19 is activated by a gradient controller 28. Furthermore, the scanner 13 has a radio-frequency (RF) antenna 20, which, in the case shown, is a body coil permanently integrated into the scanner 13, and an RF controller 29 that operates the RF antenna 20 so as to radiate RF sequences into an examination space, which is essentially formed by the patient receiving area 14. Each radiated RF sequence causes the magnetization of certain nuclear spins in the patient 15 to deviate from the basic magnetic field 18 by an amount known as a flip angle. As these excited nuclear spins relax and return to the steady state, they emit MR signals, which are also RF signals. The RF antenna 20 is further designed to receiving the MR signals from the patient 15. The magnetic resonance apparatus 11 further has a local coil 35, which is positioned on a region of the body of the patient 15 to be examined for receiving the MR signals.

The magnetic resonance apparatus 11 shown can naturally have further components that magnetic resonance apparatuses usually have. The general operation of a magnetic resonance apparatus is known to those skilled in the art, so a more detailed description is not necessary herein.

The apparatus 11 also has a computer 24. The computer 24 controls the magnetic resonance apparatus 11. The computer can be connected to a display unit 25 and an input unit 26. Preparatory information for the preparation of the magnetic resonance imaging can be provided to a user on the display unit 25. Via the input unit 26, information and/or parameters for the preparation of the magnetic resonance imaging can be entered. The display unit 25 and the input unit 26 can also be embodied as a combined touch interface. A projector 37 is also shown in FIG. 1, for projection of projection data onto a body surface of the patient 15 or onto the local coil 35.

The apparatus 11 further has a time-of-flight camera 36, which is designed for acquisition of a depth map of the patient 15 or of the local coil 35. The time-of-flight camera 36 is positioned in the examination room, in which the magnetic resonance apparatus 11 is also located, preferably on the ceiling of the examination room.

The magnetic resonance apparatus 11, the computer 24 and the time-of-flight camera 36, collectively operate so as to implement the inventive method for provision of preparatory information.

Figure 2:
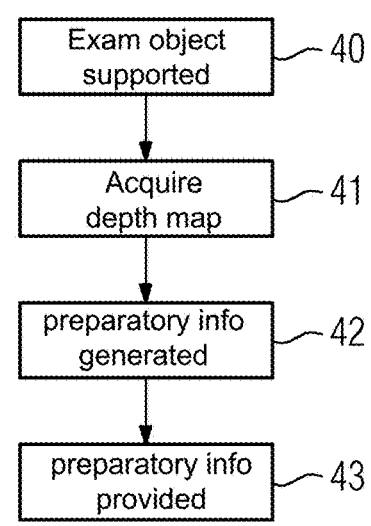
FIG. 2 is a flowchart of a first embodiment of the inventive method.

FIG. 2 shows a flowchart of a first embodiment of the inventive method for provision of preparatory information for preparation of magnetic resonance imaging of an examination object 15 by the magnetic resonance apparatus 11.

In a first method step 40, the examination object 15 is supported on the patient support 16 of the magnetic resonance apparatus 11.

In a further method step 41, a depth map of the examination object 15 supported on the patient support 16 is acquired by the time-of-flight camera 36.

In a further method step 42, preparatory information for the preparation of the magnetic resonance imaging is generated by the computer 24 using the acquired depth map.

In a further method step 43, the preparatory information is provided by the computer 24 and/or the display unit 25 and/or the projector 37.

Figure 3:
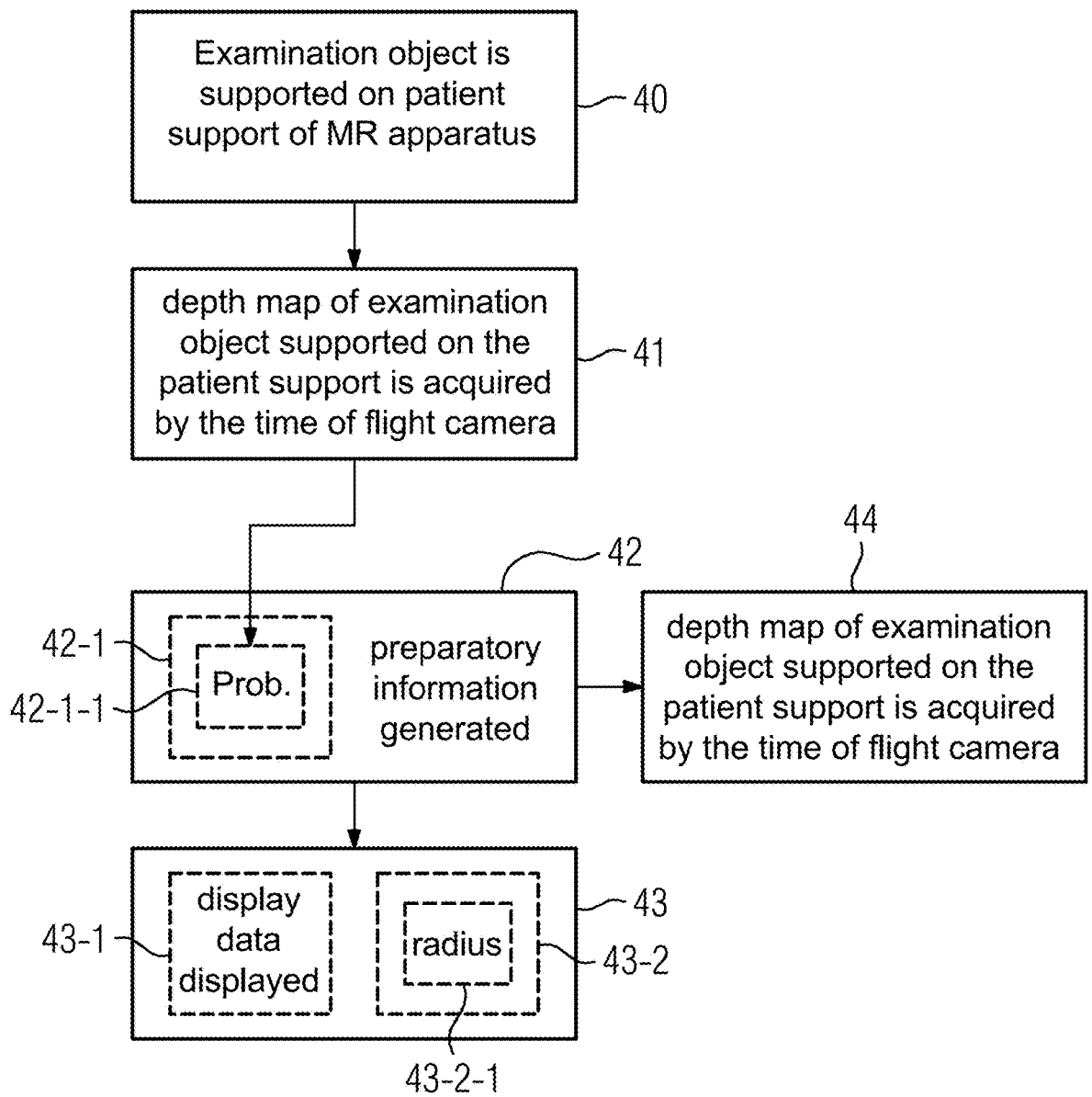
FIG. 3 is a flowchart of a second embodiment of the inventive method.
Figure 4:
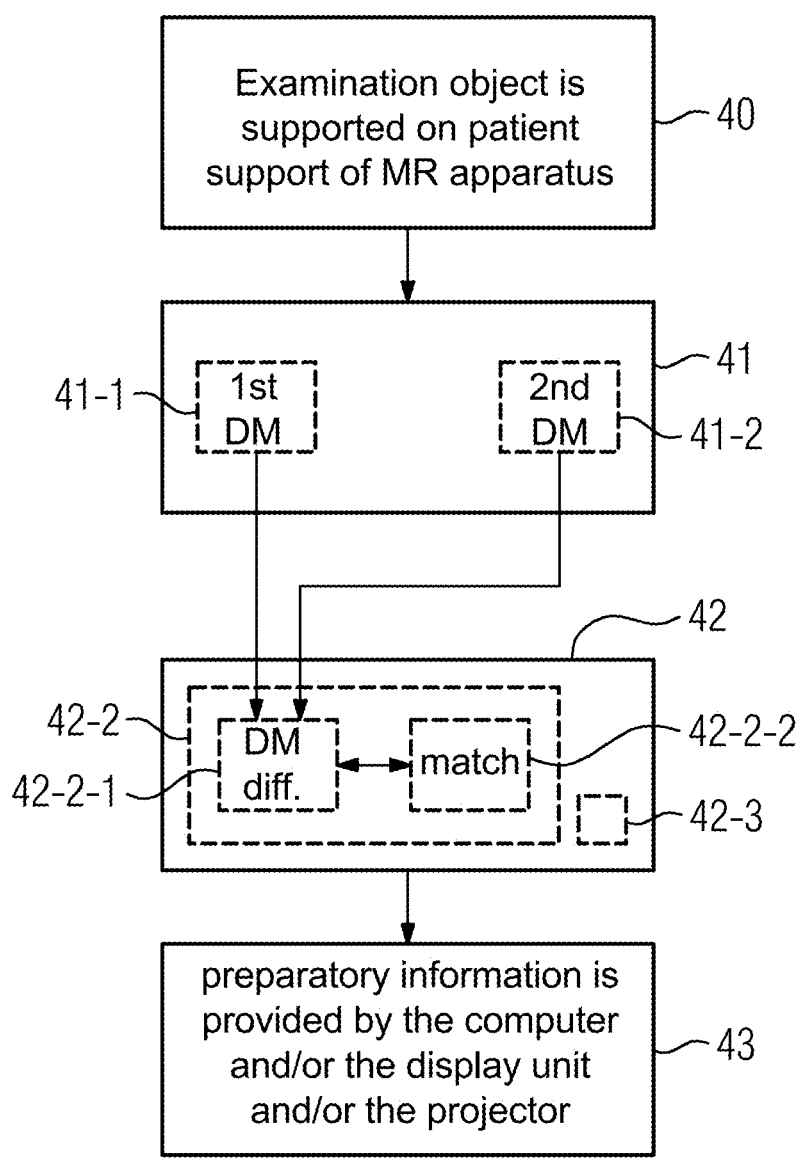
FIG. 4 is a flowchart of a third embodiment of the inventive method.
Figure 5:
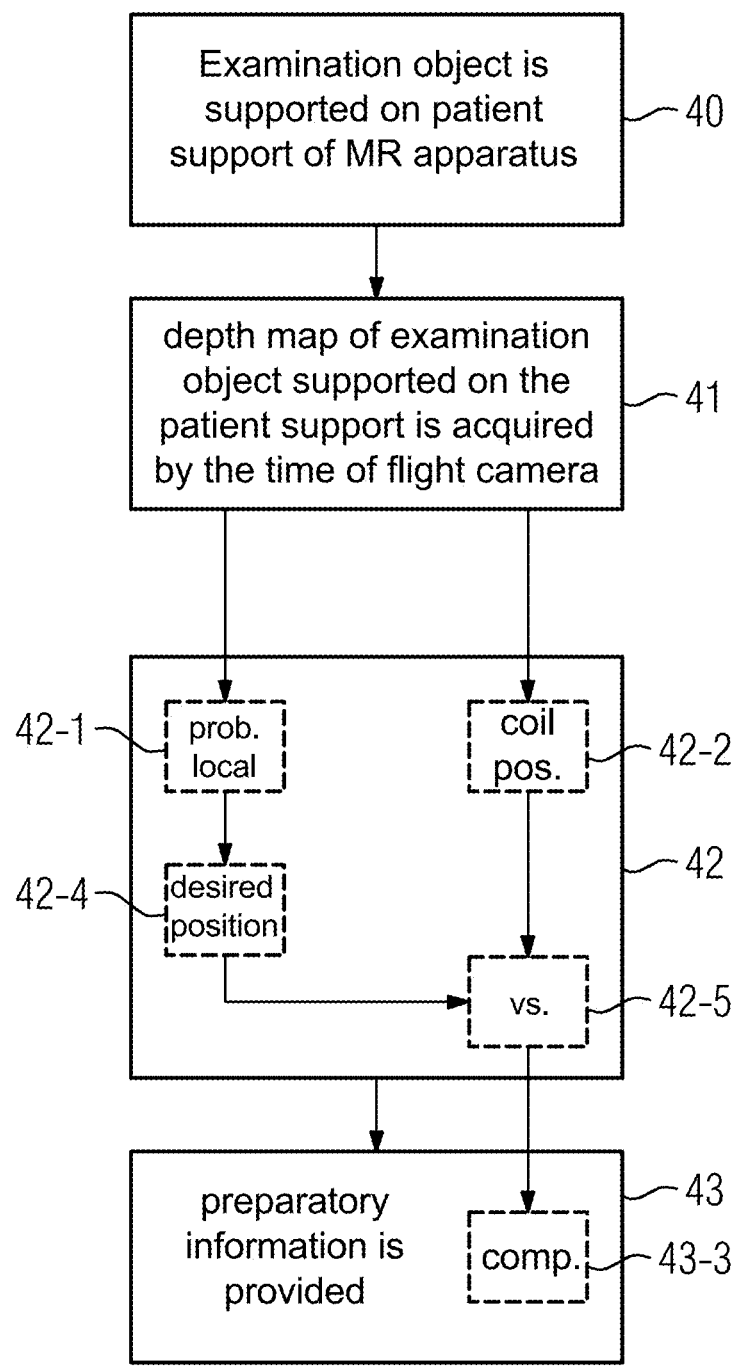
FIG. 5 is a flowchart of a fourth embodiment of the inventive method.

The following descriptions of the embodiments of FIG. 3 to FIG. 5 are essentially restricted to the differences from the exemplary embodiment in FIG. 2, wherein, as regards method steps that remain the same, the description of the exemplary embodiment in FIG. 2 applies. Method steps that essentially remain the same are labeled with the same reference characters.

The embodiments of the inventive method shown in FIG. 3 to FIG. 5 essentially include the method steps 40, 41, 42, 43 of the first embodiment of the inventive method in accordance with FIG. 2. The embodiments of the inventive method shown in FIG. 3 to FIG. 5 have additional method steps and substeps. Also conceivable is an alternate method sequence to that shown in FIG. 3 to FIG. 5, which only has some of the additional method steps and/or substeps shown in FIG. 3 to FIG. 5. Naturally an alternate method sequence to FIG. 3 to FIG. 5 can also have additional method steps and/or substeps.

FIG. 3 shows a flowchart of a second embodiment of the inventive method for provision of preparatory information for preparation of magnetic resonance imaging of an examination object 15 by the magnetic resonance apparatus 11.

In the case shown in FIG. 3, the establishment of the preparatory information has a substep 42-1, in which there is a computation of a probability of localization of an organ in a body of the examination object to be examined in the magnetic resonance imaging using the depth map. This substep 42-1 can have a further substep 42-1-1, in which the computation of the probability of localization of the organ to be examined involves a matching of a body model, which represents information about a localization of the organ to be examined in the body model, to the examination object while using the depth map.

There are now two possibilities for the provision of the preparatory information in the further method step 43, which can be realized in two different substeps 43-1, 43-2. The two different substeps 43-1, 43-2 can be carried out in this case independently of one another, or combined.

In a first substep 43-1, the provision of the preparatory information can comprise a display of display data, which are created based on the probability of localization of the organ to be examined, on the display unit 25 together with a display of a representation of a human body. In a second substep 43-2, the provision of the probability of localization can be as a projection of projection data, which are created based on the probability of localization of the organ to be examined, onto a body surface of the examination object by the projector 37. In this case, in further substep 43-2-1, at least one confidence radius can be projected onto the body surface of the examination object as projection data, wherein the at least one confidence radius designates the localization probability of the organ to be examined.

On the basis of the established probability of localization, in accordance with FIG. 3, the patient support 16 of the magnetic resonance apparatus 11 can be moved in further method step 44 such that the organ to be examined is automatically positioned in an isocenter of the magnetic resonance apparatus 11 for the magnetic resonance imaging.

FIG. 4 shows a flowchart of a third embodiment of the inventive method for provision of preparatory information for preparation of magnetic resonance imaging of an examination object 15 by the magnetic resonance apparatus 11.

In the case shown in FIG. 4, the depth map acquired in the method step 41 maps the local coil 35, which is provided for receiving magnetic resonance signals during the magnetic resonance imaging of the examination object. In this way, the generation of the preparatory information in a substep 42-2 of the further method step 42 includes establishment of a position of the local coil 35 on the basis of the depth map.

For this purpose, the acquisition of the depth map includes, in a first substep 41-1 of the further method step 41, acquisition of a first depth map in the time before a positioning of the local coil 35 for the magnetic resonance imaging and, in a second substep 41-2 of the further method step 41, acquisition of a second depth map in the time after the positioning of the local coil 35 for the magnetic resonance imaging. The establishment of the position of the local coil 35 then involves, in a substep 42-2-1 of the substep 42-2, a determination of differences between the first depth map and the second depth map. The establishment of the position of the local coil 35 in a substep 42-2-2 of the substep 42-2 here can be a matching of a geometrical model of the local coil 35 to the differences between the first depth map and the second depth map.

In the further method step 42, in a further substep 42-3, the position of a further local coil can also be determined. If a number of local coils are provided for acquisition of the magnetic resonance signals during the magnetic resonance imaging of the examination object 15, the depth map is used to establish the respective positions of these multiple local coils. For this purpose, different markers are respectively attached to a surface of each of the local coils, which are recognized in an image acquired by the time-of-flight camera 36.

As an alternative, the position of the local coil 35 can be established using a body model, which is matched to the examination object 15. For establishing the position of the local coil 35, differences between the depth map and the body model matched to the examination object 15 are determined. It is then not necessary to acquire two depth maps from the examination object to determine the position of the local coil 35.

FIG. 5 shows a flowchart of a fourth embodiment of the inventive method for provision of preparatory information for preparation of magnetic resonance imaging of an examination object 15 by the magnetic resonance apparatus 11.

FIG. 5 shows an example of how parts of the second embodiment of the inventive method in accordance with FIG. 3 and parts of the third embodiment of the inventive method in accordance with FIG. 4 can be usefully combined with one another. Thus, in accordance with FIG. 5, the substep 42-1 of the further method step 42 in accordance with FIG. 2 and the substep 42-2 of the further method step in accordance with FIG. 3 are performed. The establishment of preparatory information thus includes the computation of the probability of localization of the organ to be examined and the establishment of the position of the local coil 35.

In a further substep 42-4 of the further method step 42, a desired position for the local coil is now established on the basis of the computed probability of localization of the organ to be examined. The establishment of the preparatory information comprises a comparison of the established position of the local coil 35 with a desired position for the local coil 35 for receiving magnetic resonance signals from the organ to be examined in a further substep 42-5 of the further method step 42.

The provision of the preparatory information in the further method step 43 can then be an output of a suggestion for repositioning of the local coil 35 based on a result of the comparison in a substep 43-3 of the further method step 43.

The method steps of the inventive method shown in FIGS. 2-5 are carried out by the computer 24. To this end the computer 24 has the required software and/or computer programs, which are stored in a memory of the computer 24. The software and/or computer programs have program code designed to carry out the inventive method when the computer program and/or the software is executed in the computer 24.

Figure 6:
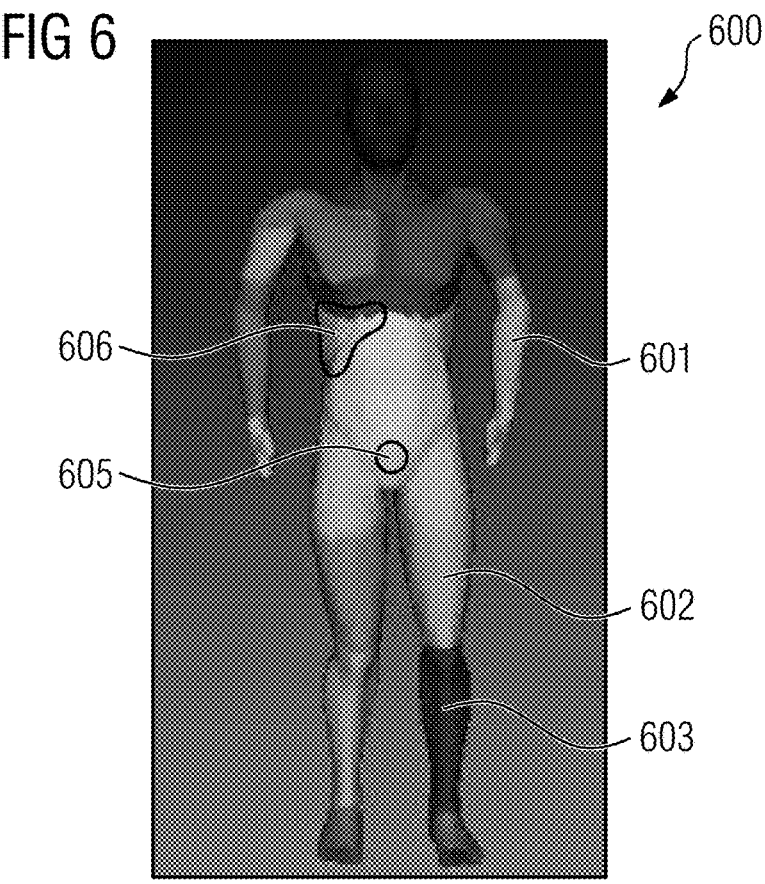
FIG. 6 shows an example of a body model for matching to the examination object using the depth map, in accordance with the invention.

FIG. 6 shows an example of a body model 600 for matching to the examination object 15 using the depth map. The body model 600 shown in FIG. 6 can accordingly be used in the substep 42-1-1 of FIG. 3 for computing the probability of localization of the organ to be examined.

Figure 7:
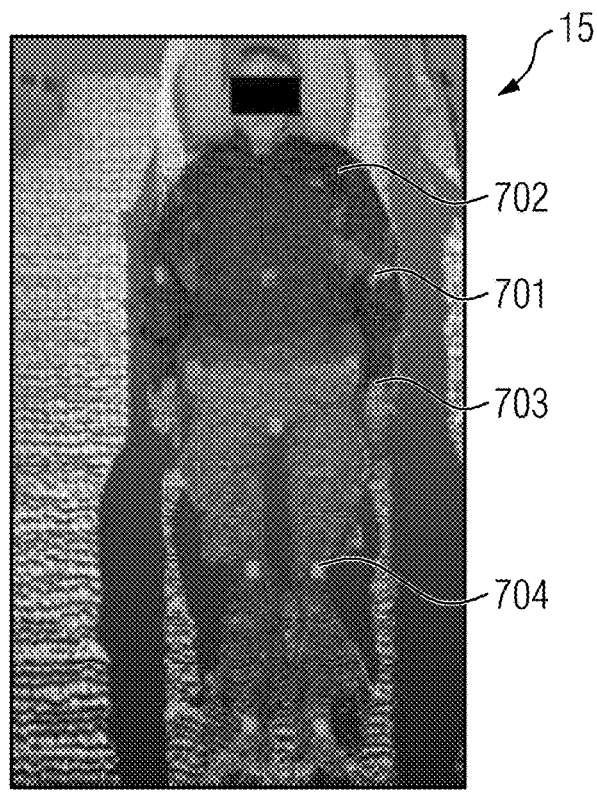
FIG. 7 shows an example for positioning landmarks for the matching of the body model to the examination object, in accordance with the invention.

In the case shown in FIG. 6, the body model 600 is embodied as a three-dimensional standard model of a human body. The body model 600 has contour information of the human body, which in this way can be matched especially easily to the depth map, which has been acquired from the examination object 15. Landmarks 701, 702, 703, 704 can be used for the matching, for example as shown in FIG. 7. For the matching the body model 600 advantageously comprises different body segments 601, 602, 603, for example an arm segment 601, an upper leg segment 602 and a lower leg segment 603, which can be matched independently of one another, by the corresponding landmarks 701, 702, 703, 704, to the examination object 15.

In addition to the contour information, the body model 600 comprises information about the localization of at least one organ 605, 606, in the case shown for example the prostate 605 and the liver 604. This information can include, for example, statistical localization probabilities of the at least one organ 605, 606. In this way, based on the matching of the body model 600 to the examination object 15, the information about the localization of the organ to be examined can be matched to the patient-specific circumstances of the support of the examination object 15. The information about the localization of the at least one organ 605, 606 in the body model 606 is in particular coupled to the contour information of the body model 600, in particular the body segments 601, 602, 603, so that during matching of the contour information of the body model 600 to the examination object 15, the information about the localization of the at least one organ 605, 606 can also be matched to the examination object 15.

FIG. 7 shows an example for positioning landmarks 701, 702, 703, 704 for the matching of the body model 600 to the examination object 15. The landmarks 701, 702, 703, 704 can be defined in the body model 600, for example in a body model 600 in accordance with FIG. 6, and can be recognized in the examination object 15 by means of a suitable detection algorithm or manually.

The configuration of the landmarks 701, 702, 703, 704 shown in FIG. 7 is naturally only to be seen as an advantageous example. Inter alia, a first landmark 701 is defined on an elbow of the examination object 15, a second landmark 702 on a shoulder of the examination object 15, a third landmark 703 on a hand of the examination object 15 and a fourth landmark 704 on a knee of the examination object 15. Naturally, further landmarks not mentioned in the text are defined.

Figure 8:
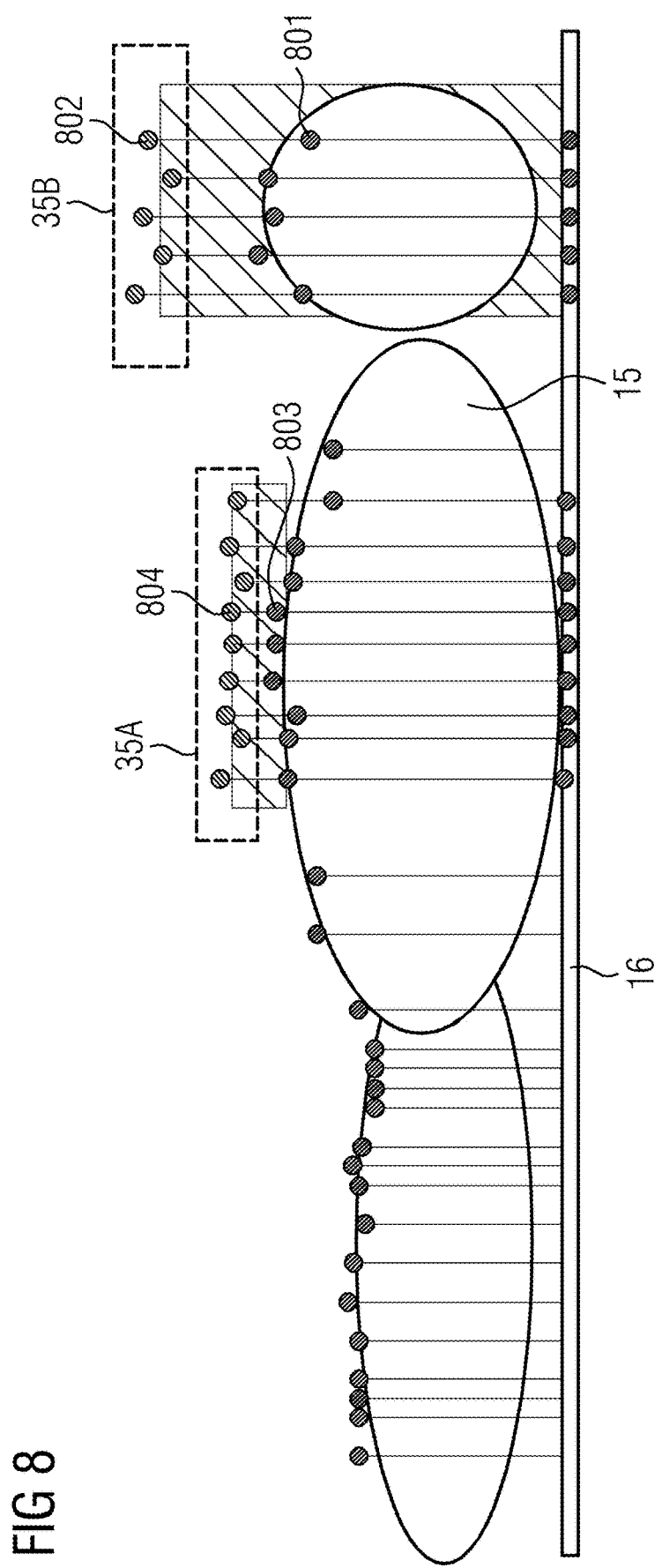
FIG. 8 shows examples of differences between a first depth map and a second depth map, in cross-section, in accordance with the invention.

FIG. 8 shows exemplary differences between a first depth map 801, 803 and a second depth map 802, 804 in cross-section.

Shown in FIG. 8 is a sagittal section through the examination object 15, which is positioned on the patient support 16. Positioned on the examination object is a first local coil 35A, which is formed by a flexible surface coil, and a second local coil 35B, which is formed by a head coil.

In first substep 41-1 of the further method step 41 in accordance with FIG. 4, a first depth map 801, 803 has been acquired in the time before the positioning of the local coils 35A, 35B for the magnetic resonance imaging of examination object 15. The first depth map 801, 803 accordingly only maps the body surface of the examination object 15. The first depth map 801, 803 in this case comprises a number of sampling points, of which some are shown in FIG. 8 and two are labeled by way of example with reference characters.

In second substep 41-2 of the further method step 41 in accordance with FIG. 4, a second depth map 802, 804 has been acquired in the time after the positioning of the local coils 35A, 35B for the magnetic resonance imaging of examination object 15. The second depth map 802, 804 accordingly comprises depth information of the local coils 35A, 35B positioned on the examination object 15. The second depth map 802, 804 in this case comprises a number of sampling points, of which some are shown in FIG. 8 and two are labeled by way of example with reference characters.

It can be seen in FIG. 8 that the second depth map 802, 804 includes depth information that, in the region of the local coils 35A, 35B, differs from the depth information the first depth map 801, 803. In this way, a determination of the differences between the first depth map 801, 803 and the second depth map 802, 804 in a substep 42-2-1 of the substep 42-2 of FIG. 4 serves as a basis for the isolation of the local coils 35A, 35B.

Figure 9:
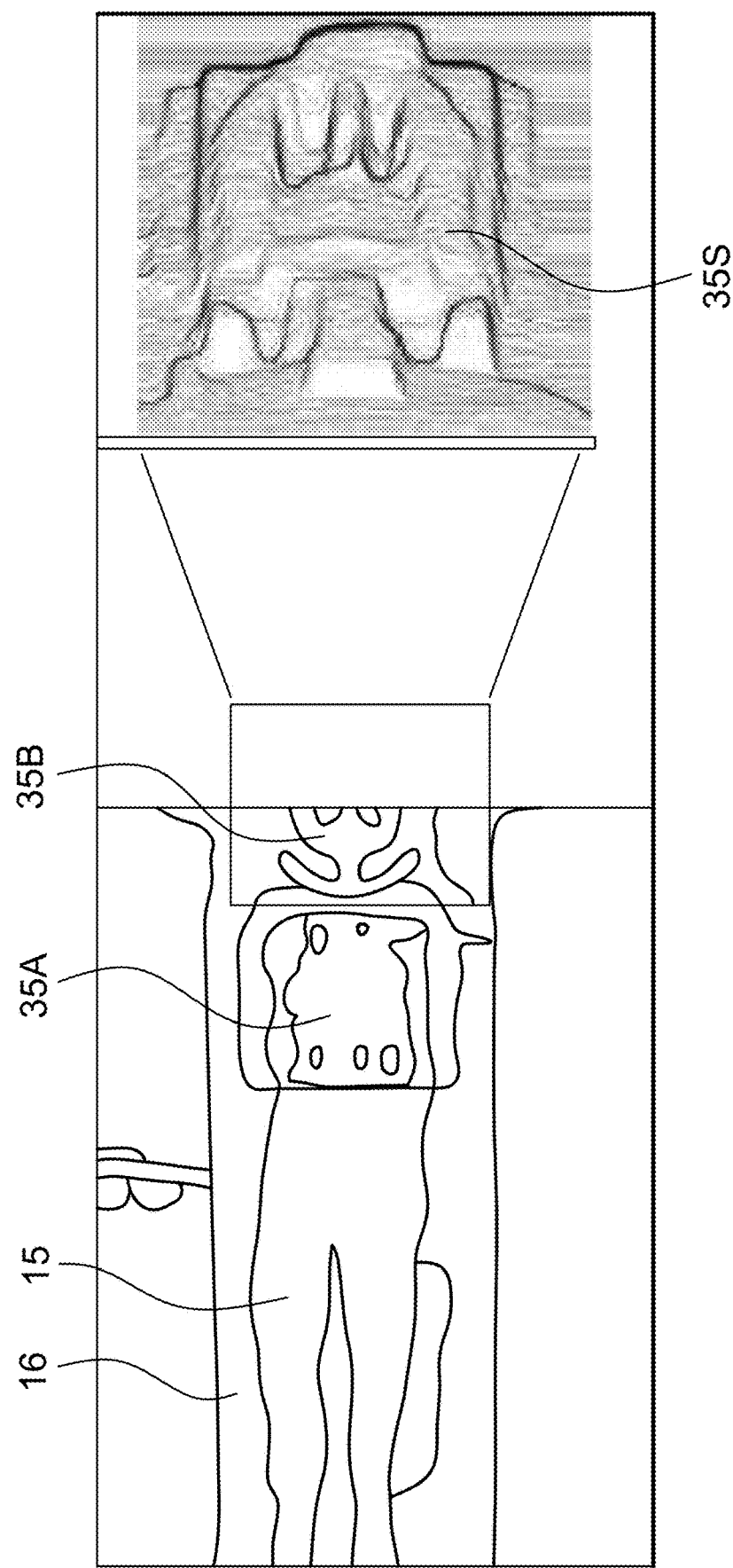
FIG. 9 shows examples of differences between a first depth map and a second depth map in cross-section, in accordance with the invention.

FIG. 9 shows exemplary differences between a first depth map 801, 803 and a second depth map 802, 804 in a view from above.

In this case, the same examination step as in FIG. 8 is shown in FIG. 9. FIG. 9 shows a view from above of differences between the first depth map 801, 803 and the second depth map 802, 804 defined in a substep 42-2-1 of the substep 42-2 of FIG. 4.

In FIG. 9 the first local coil 35A and the second local coil 35B are shown highlighted, just as they appear in the differences between the first depth map 801, 803 and the second depth map 802, 804. By suitable operators, such as threshold value operators and/or clustering operators, a pre-segmentation of the local coils 35A, 35B is possible. A segmented second local coil 35S is shown in the right section of the image from FIG. 9.

Figure 10:
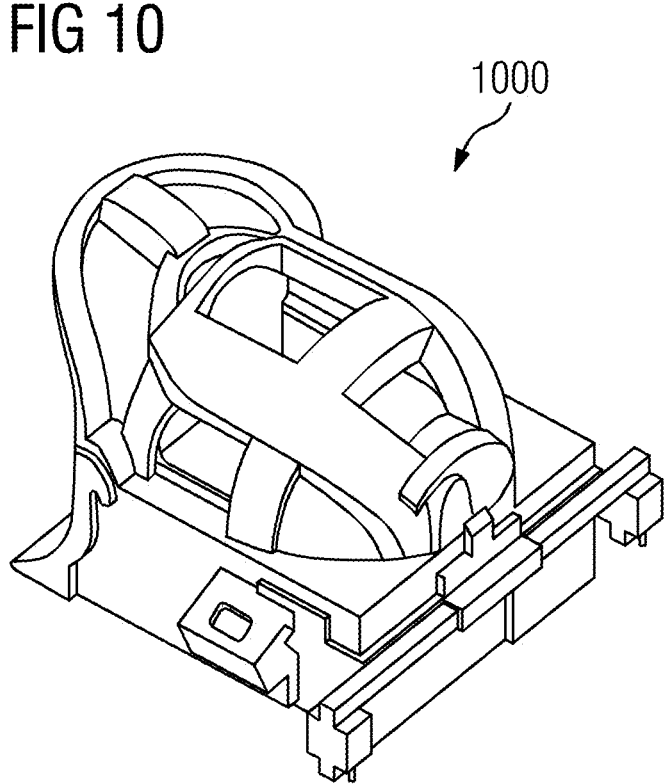
FIG. 10 shows an example of a geometrical model of a local coil for matching to the differences between the first depth map and the second depth map, in accordance with the invention.

Furthermore, the establishment of the position of the local coils 35A, 35B in a substep 42-2-2 of the substep 42-2 of FIG. 4 can comprise a matching of a geometrical model of the local coil 35A, 35B, for example of a geometrical model 1000 of the head coil shown in FIG. 10, to the differences between the first depth map 801, 803 and the second depth map 802, 804.

FIG. 10 shows a possible geometrical model 1000 of a local coil 35B for matching to the differences between the first depth map and the second depth map. Shown in FIG. 10 in this case is an example of a geometrical model 1000 of the second local coil 35B in accordance with FIG. 8 and FIG. 9, i.e. the head coil.

Figure 11:
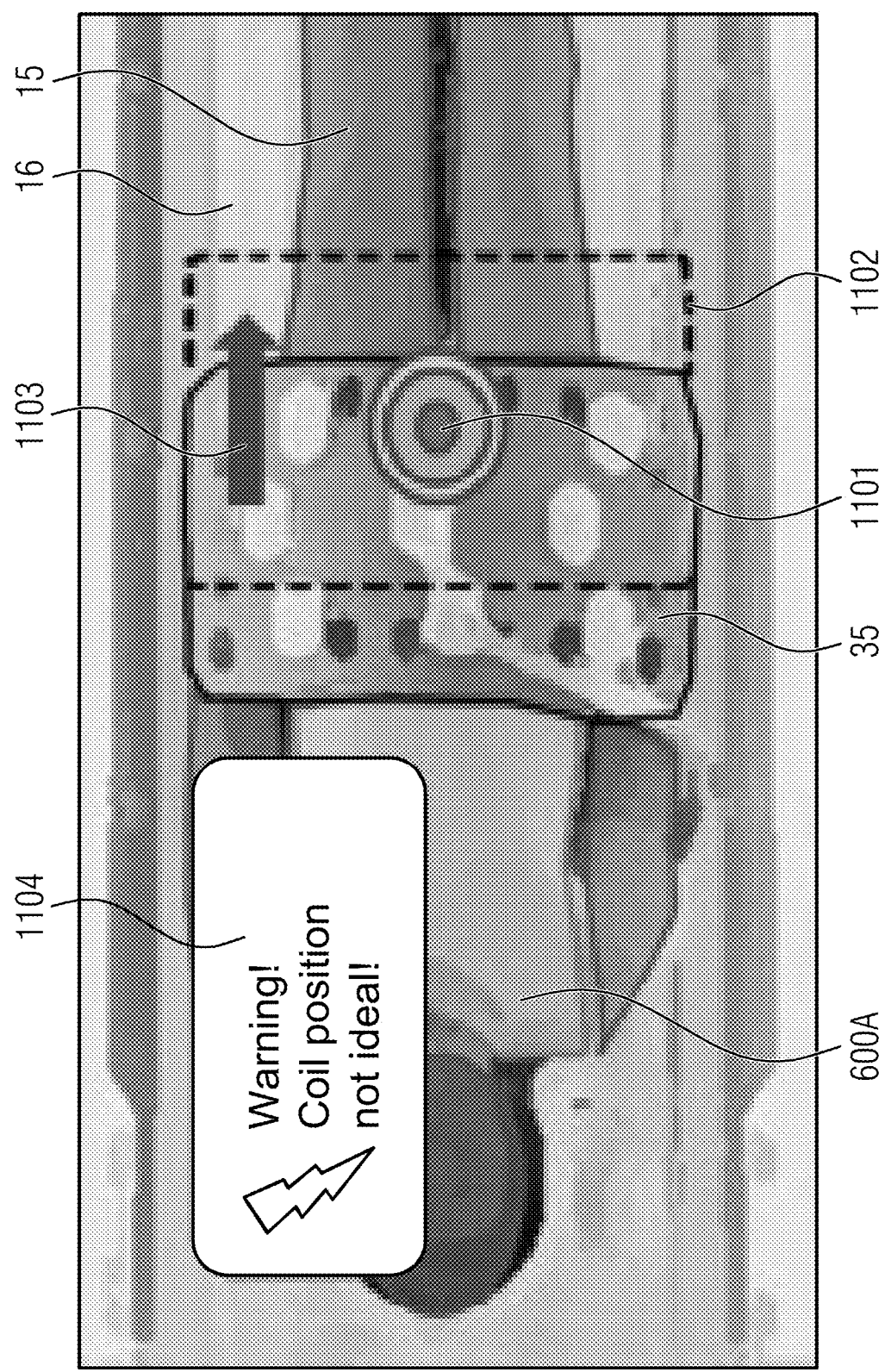
FIG. 11 shows an example of an output of a suggestion for repositioning of a local coil, in accordance with the invention.

FIG. 11 shows an example of the output of a suggestion 1103, 1104 for repositioning of a local coil 35. This suggestion 1103, 1104 can be output for example in accordance with FIG. 5 in the substep 43-3 of the further method step 43.

In the case shown in FIG. 11, the examination object 15 is supported on the patient support 16 together with a local coil 35 embodied as a flexible surface coil. A body model 600A has been matched to the examination object 15, in order to determine the highest probability of localization 1101 of the organ to be examined, in the case shown in FIG. 11, the prostate. The highest probability of localization 1101 is projected in FIG. 11 in the form of confidence radii onto the examination object 15.

In FIG. 11 the current position 1101 of the local coil 35 has already been recognized in the depth map. It is clear that the local coil 35, in its current position 1101, is not positioned centered above the highest probability of localization 1101 of the prostate. Instead, on the basis of the highest probability of localization 1101, a desired position 1102 for the local coil 35 has already been computed, as described in the further substep 42-4 of the further method step 42 of FIG. 5.

A comparison between the established current position 1101 of the local coil 35 and the desired position 1102 for the local coil 1102 has been carried out, as in the further substep 42-5 of the further method step 42 of FIG. 5. The result of the comparison is that the local coil 35 must be repositioned in the direction of the feet of the examination object 15, wherein the center of the local coil 35 should be supported above the highest probability of localization 1101 of the prostate.

Accordingly a suitable suggestion 1103, 1104 for repositioning of the local coil 35 can be output to the operating personnel. FIG. 11 shows examples of two possibilities for the suggestion 1103, 1104. Naturally these two possibilities can also be used separately from one another and other possibilities for the suggestion are also conceivable. In accordance with FIG. 11, the first possibility for the suggestion 1103 makes provision for the projection or the display of a shift vector. The second possibility for the suggestion 1104 makes provision for the output of a warning to the operating personnel.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for providing preparatory information for preparation of magnetic resonance (MR) imaging of an examination object comprising:
   supporting the examination object on a patient support of an MR data acquisition scanner, said MR data acquisition scanner including a local coil to be used in said MR imaging of the examination object;
   operating a time-of-flight camera in order to acquire a depth map of the examination object while supported on the patient support to map said local coil, and providing said depth map to a computer, wherein acquiring said depth map includes acquiring a first depth map at a time before positioning said local coil and acquiring a second depth map at a time after positioning said local coil;
   in said computer, establishing preparatory information, using based on the acquired depth map to establish a position of a local coil relative to the examination object, for preparation of MR imaging of the examination object by operation of said MR data acquisition scanner, said preparatory information including said position of the local coil, wherein establishing said position of said local coil includes determining differences between said first depth map and said second depth map and matching a geometric model of said local coil to said differences between said first depth map and said second depth map; and
   providing said preparatory information in electronic form as an output from said computer.

2. A method as claimed in claim 1 comprising establishing said preparatory information by using said depth map to compute a probability of localization of an organ in the body of the examination object.

3. A method as claimed in claim 2 comprising computing said probability of localization of said organ by implementing a matching of the organ in the examination object, dependent on said depth map, to a body model that comprises information defining localization of said organ in said body model.

4. A method as claimed in claim 2 comprising, at a display screen in communication with said computer, displaying said preparatory information comprising said localization of said organ in a displayed representation of a human body at said display screen.

5. A method as claimed in claim 2 comprising providing said preparatory information comprising said probability of localization of said organ by projecting a representation of said probability as projection data from a projector in communication with said computer, onto a body surface of said examination object.

6. A method as claimed in claim 5 comprising generating, in said projection data, at least one confidence radius dependent on said localization probability, and projecting said confidence radius on said body surface of the examination object with said projector.

7. A method as claimed in claim 2 comprising moving said patient support dependent on said probability of localization of said organ in order to position said organ automatically in an isocenter of said MR data acquisition scanner.

8. A method as claimed in claim 1, wherein said local coil is one of a plurality of local coils to be used for said MR imaging of said examination object, and operating said time-of-flight camera to acquire said depth map so as to include all of said plurality of local coils, and establishing said preparatory information, using said depth map, so as to include a designation of respective positions of each of said plurality of local coils.

9. A method as claimed in claim 1 comprising establishing the position of the local coil using a body model corresponding to the examination object, by identifying differences between said depth map and said body model.

10. A method as claimed in claim 1 comprising:
establishing said preparatory information by using said depth map to compute a probability of localization of an organ in the body of the examination object,
establishing said preparatory information by implementing a comparison between the established position of the local coil and a desired position of the local coil for said MR imaging, and
establishing the desired position of the local coil from said computed probability of localization of the organ.

11. A method as claimed in claim 10 comprising providing said preparatory information so as to include output of a suggestion for repositioning the local coil based on said comparison.

12. A magnetic resonance (MR) imaging apparatus comprising:
an MR data acquisition scanner comprising a patient support adapted to receive and support an examination object thereon, and a local coil to be used in said MR imaging of the examination object;
a time-of-flight camera with a field of view that encompasses the examination object on the patient support;
a computer configured to operate the time-of-flight camera in order to acquire a depth map of the examination object while supported on the patient support to map said local coil, wherein acquiring said depth map includes acquiring a first depth map at a time before positioning said local coil and acquiring a second depth map at a time after positioning said local coil;
said computer being configured to establish preparatory information, based on the use the acquired depth map to establish a position of a local coil relative to the examination object, for preparation of MR imaging of the examination object by operation of said MR data acquisition scanner, said preparatory information including said position of the local coil, wherein establishing said position of said local coil includes determining differences between said first depth map and said second depth map and matching a geometric model of said local coil to said differences between said first depth map and said second depth map; and
said computer being configured to provide said preparatory information in electronic form as an output from said computer.

13. A non-transitory, computer-readable data storage medium encoded with programming instructions, said storage medium being loaded into a computer system of a magnetic resonance (MR) imaging apparatus comprising an MR data acquisition scanner with a patient support, a local coil to be used in MR imaging of an examination object, and a time-of-flight camera, said programming instructions causing said computer system to:
operate the time-of-flight camera in order to acquire a depth map of an examination object while supported on the patient support to map said local coil, wherein acquiring said depth map includes acquiring a first depth map at a time before positioning said local coil and acquiring a second depth map at a time after positioning said local coil;
establish preparatory information, based on the use the acquired depth map to establish a position of the local coil relative to the examination object, for preparation of MR imaging of the examination object by operation of said MR data acquisition scanner, said preparatory information including said position of the local coil, wherein establishing said position of said local coil includes determining differences between said first depth map and said second depth map and matching a geometric model of said local coil to said differences between said first depth map and said second depth map; and
provide said preparatory information in electronic form as an output from said computer system.

14. A method for providing preparatory information for preparation of magnetic resonance (MR) imaging of an examination object comprising:
supporting the examination object on a patient support of an MR data acquisition scanner, said MR data acquisition scanner including a local coil to be used in said MR imaging of the examination object;
operating a time-of-flight camera in order to acquire a depth map of the examination object while supported on the patient support to map said local coil, and providing said depth map to a computer;
in said computer, establishing preparatory information, based on the acquired depth map to establish a position of the local coil relative to the examination object, for preparation of MR imaging of the examination object by operation of said MR data acquisition scanner, said preparatory information including said position of the local coil, wherein establishing the position of the local coil includes identifying differences between said depth map and a body model corresponding to the examination object; and
providing said preparatory information in electronic form as an output from said computer.

15. A magnetic resonance (MR) imaging apparatus comprising:

an MR data acquisition scanner comprising a patient support adapted to receive and support an examination object thereon, and a local coil to be used in said MR imaging of the examination object;

a time-of-flight camera with a field of view that encompasses the examination object on the patient support;

a computer configured to operate the time-of-flight camera in order to acquire a depth map of the examination object while supported on the patient support to map said local coil;

said computer being configured to establish preparatory information, based on the acquired depth map to establish a position of the local coil relative to the examination object, for preparation of MR imaging of the examination object by operation of said MR data acquisition scanner, said preparatory information including said position of the local coil, wherein establishing the position of the local coil includes identifying differences between said depth map and a body model corresponding to the examination object; and said computer being configured to provide said preparatory information in electronic form as an output from said computer.

16. A non-transitory, computer-readable data storage medium encoded with programming instructions, said storage medium being loaded into a computer system of a magnetic resonance (MR) imaging apparatus comprising an MR data acquisition scanner with a patient support, a local coil to be used in MR imaging of an examination object, and a time-of- flight camera, said programming instructions causing said computer system to:

operate the time-of-flight camera in order to acquire a depth map of the examination object while supported on the patient support to map said local coil;

establish preparatory information, based on the acquired depth map to establish a position of the local coil relative to the examination object, for preparation of MR imaging of the examination object by operation of said MR data acquisition scanner, said preparatory information including said position of the local coil, wherein establishing the position of the local coil includes identifying differences between said depth map and a body model corresponding to the examination object; and provide said preparatory information in electronic form as an output from said computer system.

\* \* \* \* \*